(12) United States Patent
Jabir et al.

(10) Patent No.: US 10,996,182 B2
(45) Date of Patent: May 4, 2021

(54) MEMRISTOR BASED SENSOR

(71) Applicants:Oxford Brookes University, Oxford (GB); University of Rome Tor Vergata, Rome (IT)

(72) Inventors: Abusaleh Jabir, Oxford (GB); Marco Ottavi, Rome (IT); Jimson Mathew, Oxford (GB); Eugenio Martinelli, Rome (IT); Corrado Di Natale, Rome (IT); Adedotun Adeyemo, Oxford (GB)

(73) Assignee: OXFORD BROOKES UNIVERSITY, Oxford (GB)

( * ) Notice: Subject to any disclaimer, the term of this patent is extended or adjusted under 35 U.S.C. 154(b) by 15 days.

(21) Appl. No.: 16/339,493

(22) PCT Filed: Oct. 4, 2017

(86) PCT No.: PCT/IB2017/056113
§ 371 (c)(1),
(2) Date: Apr. 4, 2019

(87) PCT Pub. No.: WO2018/065914
PCT Pub. Date: Apr. 12, 2018

(65) Prior Publication Data
US 2019/0227017 A1   Jul. 25, 2019

(30) Foreign Application Priority Data
Oct. 4, 2016 (GB) ..................... 1616837

(51) Int. Cl.
*G01R 27/08* (2006.01)
*G01N 27/12* (2006.01)
(Continued)

(52) U.S. Cl.
CPC ........... *G01N 27/128* (2013.01); *G01N 27/02* (2013.01); *G01N 27/041* (2013.01); *G01N 27/06* (2013.01);
(Continued)

(58) Field of Classification Search
CPC ...... G01N 27/041; G01N 27/06; G01N 27/20; G01N 27/02; H01L 2924/00014;
(Continued)

(56) References Cited

U.S. PATENT DOCUMENTS

2005/0268699 A1* 12/2005 Papakostas ............... G01L 1/20
73/46
2007/0262962 A1* 11/2007 Xiaoping ............ G06F 3/03548
345/173
(Continued)

FOREIGN PATENT DOCUMENTS

CN   102484129 A   5/2012
CN   105637357 A   6/2016
(Continued)

OTHER PUBLICATIONS

Chinwe Nyenke and Lixin Dong; "Fabrication of a W/CuxO/Cu memristor with sub-micron holes for passive sensing of oxygen" Microelectronic Engineering [online] vol. 164 (2016), pp. 48-52. See especially figures 2 & 3 and p. 49.
(Continued)

*Primary Examiner* — Raul J Rios Russo
(74) *Attorney, Agent, or Firm* — William J. Clemens; Shumaker, Loop & Kendrick, LLP

(57) ABSTRACT

A sensor comprises a plurality of sensor elements arranged in an array. Each sensor element is memristive and has an electrical resistance characteristic related to exposure to a species to be sensed. The sensor elements are arranged to be connectable such that at least one sensor element is con-
(Continued)

nected in parallel with at least one other sensor element. By using appropriate connections, the array of sensor elements can be read.

8 Claims, 3 Drawing Sheets

(51) Int. Cl.
| | | |
|---|---|---|
| *G01N 33/00* | (2006.01) | |
| *G01N 27/04* | (2006.01) | |
| *G01N 27/06* | (2006.01) | |
| *G01N 27/20* | (2006.01) | |
| *G01N 27/02* | (2006.01) | |
| *H01L 21/66* | (2006.01) | |

(52) U.S. Cl.
CPC .............. *G01N 27/12* (2013.01); *G01N 27/20* (2013.01); *G01N 33/0031* (2013.01); *G01N 33/0062* (2013.01); *H01L 22/14* (2013.01); *H01L 2224/45015* (2013.01); *H01L 2224/45099* (2013.01); *H01L 2924/00014* (2013.01)

(58) Field of Classification Search
CPC . H01L 2224/45015; H01L 2224/45099; H01L 22/14
See application file for complete search history.

(56) References Cited

U.S. PATENT DOCUMENTS

| | | | |
|---|---|---|---|
| 2012/0032134 A1 | 2/2012 | Yang et al. | |
| 2012/0194967 A1* | 8/2012 | Keane | .................... H01C 13/00 |
| | | | 361/437 |
| 2014/0016396 A1* | 1/2014 | Mazumder | ........... G11C 13/004 |
| | | | 365/148 |
| 2016/0223490 A1 | 8/2016 | Astley et al. | |
| 2017/0356812 A1* | 12/2017 | Madden | ................. G06F 3/0446 |
| 2020/0161373 A1* | 5/2020 | Cheng | ................ G11C 13/0026 |

FOREIGN PATENT DOCUMENTS

| | | |
|---|---|---|
| WO | 2011005266 A1 | 1/2011 |
| WO | 2011133139 A1 | 10/2011 |
| WO | 2012017424 A1 | 2/2012 |
| WO | 2015183291 A1 | 12/2015 |

OTHER PUBLICATIONS

Chinwe Nyenke and Lixin Dong; "Sensing ambient oxygen using a W/CuxO/Cu memristor" Nano/Micro Engineered and Molecular Systems (NEMS), 2015, pp. 254-258. See especially figures 1 & 2 and p. 255.

Chinese Office Action dated Dec. 14, 2020.

* cited by examiner

MEMRISTOR BASED SENSOR

The present invention relates to a sensor comprising an array of memristive sensor elements, such as for sensing chemical species.

The use of a single memristor (short for 'memory-resistor') as a gas sensor has been proposed. Measurement errors could be reduced statistically by taking multiple measurements from the same sensor or from different independent sensors. However, the reliability of a measurement cannot be ascertained by taking multiple measurements from a single sensor. Taking redundant sample measurements from multiple sensors can ensure reliability.

Arrays of memristors have been proposed as a digital memory architecture. However, reading the resistance of a single memristor element in such an array when acting as a sensor is problematic because memristive elements are typically bidirectional conductors (unlike conventional semiconductor memory structures). This conductive property means that 'sneak-paths' are present (i e unintended conductive routes through the array), which can lead to erroneous sensing of the resistance of the selected memristive element in the array. When a device is used as a memory, it is only necessary to distinguish between two binary states of the memristor which may have hugely different resistance values to represent 1 and 0; consequently the presence of sneak paths is less of a problem (though it can still be a problem, and can lead to eventual degradation of the stored information). However, for chemical sensing measurement, one may need to sense a continuum of resistance values, and so the sensing margin is seriously degraded by the existence of sneak-paths. The sneak-paths also limit the maximum array size because the read margin degrades severely as the array size increases in the presence of sneak-paths.

The present invention has been devised in view of the above problems.

Accordingly, one aspect of the present invention provides a sensor comprising:
a plurality of sensor elements arranged in an array,
wherein each sensor element is memristive and has an electrical resistance characteristic related to exposure to a species to be sensed, and
wherein the sensor elements are arranged to be connectable such that at least one sensor element is connected in parallel with at least one other sensor element.

Another aspect of the invention provides a method of reading a sensor, wherein the sensor comprises a plurality of sensor elements arranged in an array, and each sensor element is memristive and has an electrical resistance characteristic related to exposure to a species to be sensed,
wherein the method comprises connecting the sensor elements such that at least one sensor element is connected in parallel with at least one other sensor element Further aspects of the invention are defined in the dependent claims.

Embodiments of the invention will now be described, by way of example only, with reference to the accompanying drawings, in which.

Memristors are known in the art as devices whose electrical resistance is changed by the electrical current that flows through the device. The resistance has a minimum value $R_{ON}$ and a maximum value $R_{OFF}$. The resistance can be switched by application of appropriate voltage or current, and is non-volatile (the resistance value is 'remembered'), so that a memristor can be used as a memory element.

Memristors can be made of various materials, such as: $TiO_2$ (for example with doped and undoped regions and with Pt electrodes); $Ag/Ag_5In_5Sb_{60}Te_{30}/Ta$; Ag-a-LSMO-Pt (Ag nano-filaments in amorphous manganite thin films); other metal oxide semiconductors, such as aluminium oxide, copper oxide, silicon oxide, zinc oxide, tantalum oxide, hafnium oxide; amorphous perovskite oxides (such as a-SrTiO$_3$); as well as other ferroelectric and doped polymeric materials, and also graphene oxide. Embodiments of the present invention are not limited to any specific material, provided the memristive property is present. A component that acts as a memristor is described herein as being memristive.

One embodiment of the invention comprises a highly dense array of nanoscale memristors, fabricated by lithographic techniques used in microelectronics such as for making memory chips (integrated circuits, ICs). The array is constructed using a crossbar architecture consisting of a set of parallel nanowires located on another set of parallel nanowires running perpendicularly to the first set. A memristor is located at every intersection point of the wires. Rows and columns are defined by the parallel sets of wires (also referred to as the bit-lines and word-lines in digital electronic memory), and each memristor is connected between the wire of one row and one column. Each memristor in the array can act as a sensor element for the overall sensor device.

Figure 1:
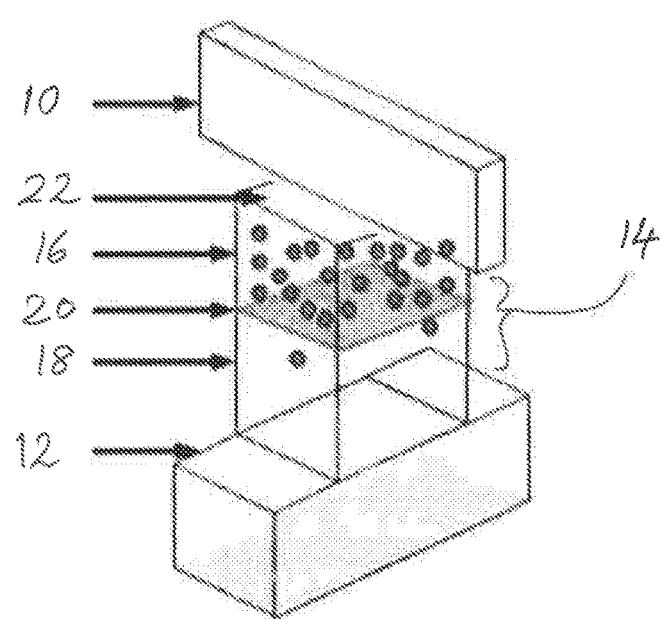
FIG. 1 is a magnified schematic illustration of a memristive sensor element in a crossbar array according to an embodiment of the invention.

FIG. 1 illustrates one memristor at one such intersection in an array. A top wire 10 runs in one direction perpendicular to a bottom wire 12, and these wires form the electrodes of the memristor 14, and can be made of, for example, platinum. The memristor 14 in this embodiment comprises a thin film of titanium oxide, comprising an upper part 16 and a lower part 18 with a doping wall 20 in between. The upper part 16 is non-stoichiometric, such as $TiO_{2-x}$, and the lower part is titanium dioxide ($TiO_2$). The upper surface 22 of the thin film is left exposed either side of the top wire 10 to allow for easy interaction between the environment to be sensed and the memristor 14.

The memristor, or a whole array of memristors on a chip, can be provided with a heater (not shown) to raise its temperature to a suitable operating temperature as necessary for the chemical species to be sensed. The heater can also stabilize the temperature to a constant value for consistent measurements.

Figure 2:
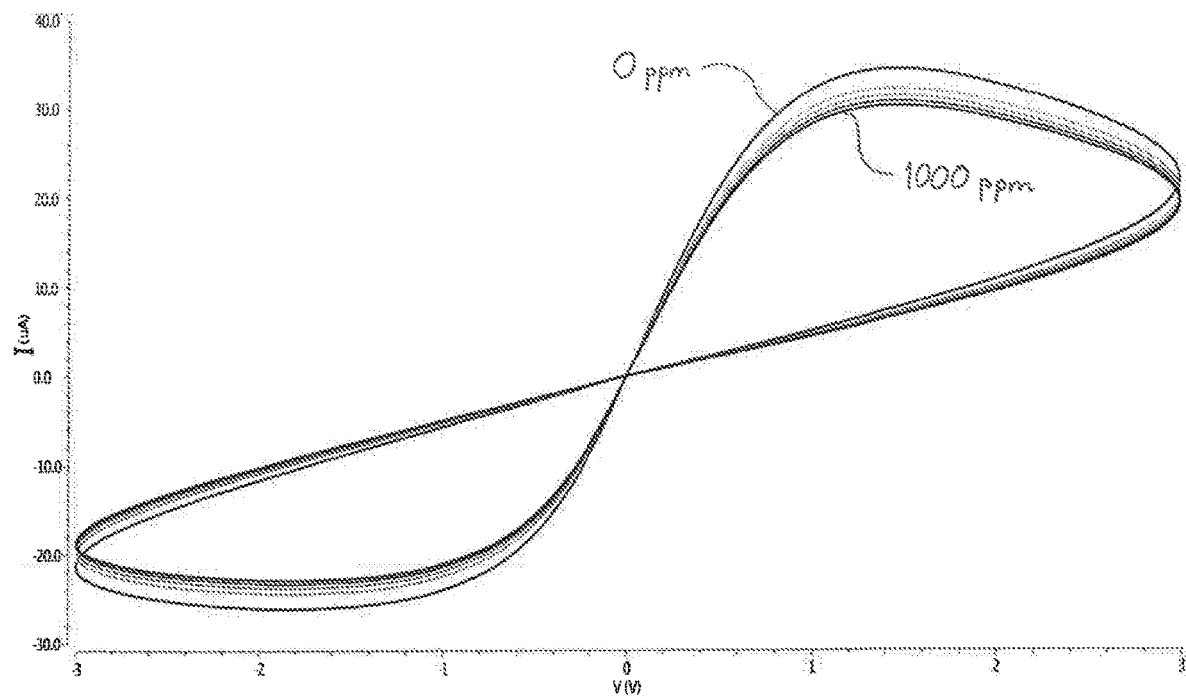
FIG. 2 shows graphs of the IV characteristics of a memristive sensor element used in an embodiment of the invention for different gas concentrations.

Adsorption of molecules on the surface 22 of the titanium oxide film produces a change in the electrical resistance characteristic of the memristor. FIG. 2 shows plots of the current versus voltage (IV) characteristics of a memristor used in an embodiment of the invention. The overall shape is characteristic of a memristor with a high resistance state (low gradient, approx. 200 kilohms) and a low resistance state (high gradient, approx. 100 ohms), and switchable between the two. A number of different plots are superimposed in FIG. 2 for different gas concentrations ranging from 0 ppm to 1000 ppm, as indicated. As can be seen, the presence of gas concentration changes the electrical resistance characteristic of the memristor. In this way, the memristor can act as a gas sensor element. The particular 'characteristic' used can be a single value, such as peak resistance, or gradient, or difference between high and low resistances, and so on; or can be a combination of multiple such values.

The gas concentration can be sensed or measured in a variety of ways, as the circumstances dictate, for example by: the absolute resistance of the memristor (in the high or low resistance states, or both); the ratio of high to low resistance; the peak current; differential resistance, and so on. The resistance characteristic measurements can be performed using DC and/or AC techniques, and with or without bias voltages. Resistance values can be calibrated against known gas concentrations, and provided as a look-up table or as an equation for the sensor to convert electrical measurements to gas concentrations.

In general, the interaction of a target chemical species with the surface of the memristor results in a change in the resistivity, and causes a change in output of the associated read circuitry (not shown). Choice of materials for the memristor, such as the oxides mentioned above, and also polymers or porphyrins, means it is possible to select the target species and sensitivity pattern of the sensor. The memristor can also be made selective to sense only one species or a specific group of species, but not others. For example, a sensor embodying the invention could be used to detect volatile compounds and gases, such as nitrogen oxides, carbon monoxide, alcohols, amines, terpenes, hydrocarbons, or ketones, and/or a variety of different gases (oxidizing or reducing). Although the embodiment above referred to sensing species in the gas phase, that is not essential to the invention; embodiments of the invention can also be used to sense liquids or species in liquids (for example ions of Hg, Ca, Pb, Cr), and as biosensors (for example for sensing pesticides, specific proteins, amino acids, or DNA). The structure and measurement technique of the sensor described herein could, in principle, be used in other embodiments to sense physical properties instead of chemical species; for example, as a thermistor for sensing temperature, or as a photoconductor for sensing light, and so on.

Figure 3:
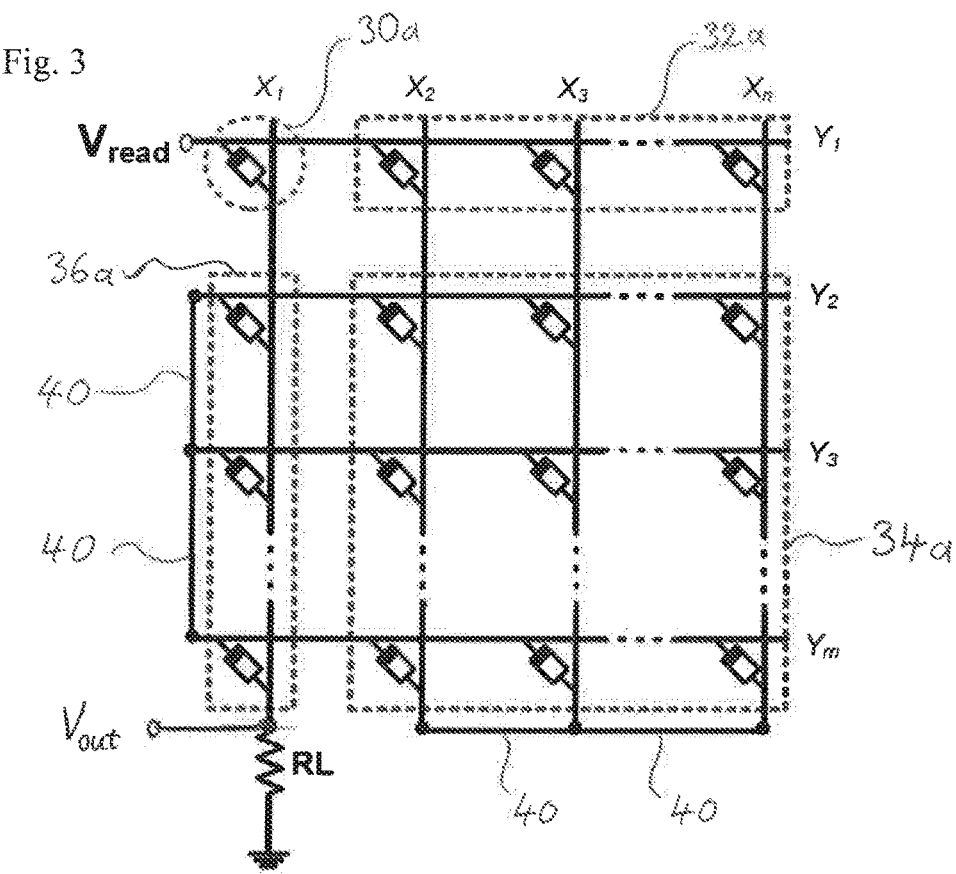
FIG. 3 is a simplified circuit diagram of a sensor comprising a two-dimensional array of memristive elements according to an embodiment of invention.
Figure 4:
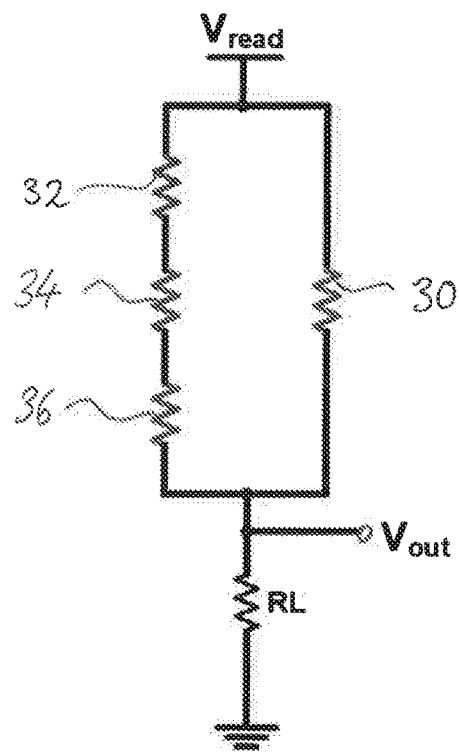
FIG. 4 is a schematic equivalent of the circuit of FIG. 3.

FIG. 3 shows the circuit of a crossbar array sensor according to an embodiment of the invention. The array is n×m with column wires X1, X2, ... Xn, and row wires Y1, Y2, ... Ym. A memristor is connected across each row/column intersection. In this embodiment, one specific memristor is selected to be read for sensing (in this case at X1, Y1, but it could be any one in the array), by connecting a read voltage Vread to the relevant row, and connecting a load resistor RL between the corresponding column wire and ground. However, as can be seen in FIG. 3, there are manifold sneak-paths between the terminal at which Vread is applied and the load resistor RL, via the other memristors (because they can conduct in either direction), in addition to conduction simply through the selected memristor at X1, Y1. This is analyzed in the equivalent circuit shown in FIG. 4, when considered in conjunction with FIG. 3. The selected memristor 30a is represented by the resistor 30 with resistance $R_{X1Y1}$. The sneak-path resistance is in parallel with the resistor 30 and comprises three components in series: (i) the resistance 32 of the memristors connected to the row Y1 (illustrated in the dotted box 32a in FIG. 3); (ii) the resistance 34 of the network of memristors indicated in the box 34a; and (iii) the resistance 36 of the memristors connected to the column X1 (illustrated in the dotted box 36a in FIG. 3). If all the unselected memristors have the same resistance R then the resistance 32 is n−1 memristors in parallel, i.e.

$$\frac{R}{(n-1)};$$

the resistance 34 is $$\frac{R}{(n-1)(m-1)};$$

and the resistance 36 is $$\frac{R}{(m-1)}.$$

The total sneak-path resistance $R_{sneak}$ is the sum of these three resistances 32, 34, 36 in series:

$$R_{sneak} = R \times \frac{m+n-1}{(m-1)(n-1)}$$

And the total resistance of the array between Vread and the fixed load resistance RL is the parallel combination of the selected memristor and the rest of the array sneak-path:

$$R_{total} = R_{X1Y1} \| R_{sneak}$$

This total resistance $R_{total}$ and the load resistance RL form a potential divider, so the $R_{total}$ value can be determined by measuring the voltage at the terminal Vout, knowing the load resistance value RL and the value of Vread (or equivalently, the whole IV characteristics of the array can be obtained by changing Vread).

The value $R_{total}$ captures information about all memristors in the array in a single reading cycle from a single point, so can be used to determine the concentration of the species being sensed. In this way, the sneak-path resistance is actually leveraged to contribute to the sensing. The structure takes advantage of the sneak-path and uses the entire array as a single sensor.

In this embodiment, the unselected row and column wires are shorted by connections 40. This can help ensure that the current has only one point of entry and exit into the array. Preferably these connections 40 are direct connections, such as low resistance wiring paths, optionally through switches or switching components. In an ideal circuit, these unselected rows and columns are at the same potential, so connections 40 are unnecessary, but in a practical very large array, these connections can help distribute the current uniformly.

In general, the memristors in the array are all set to the same state (high or low resistance), but this need not be the case. For example the 'selected' memristor can be set to be in a different state from the rest of the array. Each memristor is individually addressable.

A sequence of measurements can be performed using a different selected memristor each time, to improve the measurement accuracy and to confirm the measurement reliability. The selected memristor can be chosen in a random sequence in the array or can be cycled in a systematic sequence.

If an inconsistent measurement is obtained, it may indicate that the selected memristor for that measurement is faulty. In that case, particular rows or columns or memristors can be deselected by not making particular connections 40 and/or by setting particular adjacent memristors to a high resistance state.

In all embodiments, the circuitries for addressing the array (such as applying a voltage Vread to a desired row or column, connecting a load resistance RL), and for making connections 40 between row and column wires, and providing a Vout sensing terminal, could be hard-wired, but are preferably all made with logic circuitry integrated on the chip, for example around the periphery, as is known in the art in relation to memory chips.

Figure 5:
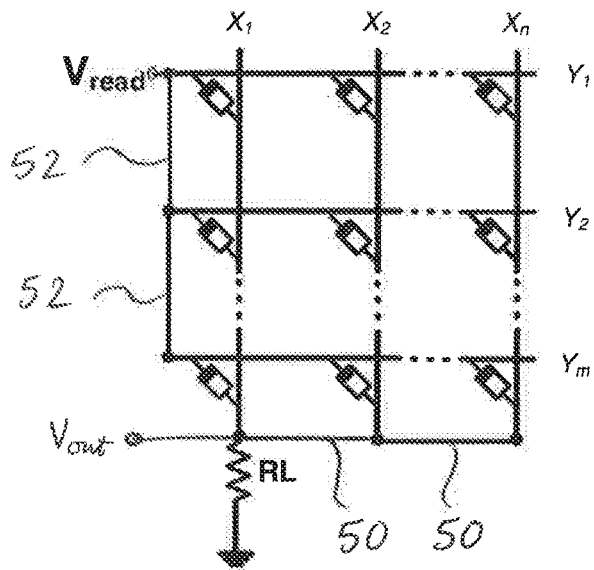
FIG. 5 is a simplified circuit diagram of a sensor comprising a two-dimensional array of memristive elements according to another embodiment of invention.

An alternative embodiment is illustrated in FIG. 5. In this case, all the column wires are connected to each other by connections 50, and all the row wires are connected to each other by connections 52. This means that all of the memristors in the array are simply in parallel with each other, and so the total resistance R total is $$\frac{R}{(n \times m)}$$

assuming all memristors have resistance R.

Figure 6:
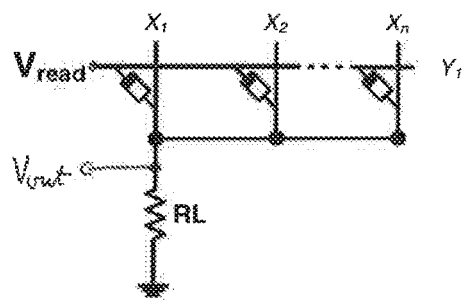
FIG. 6 is a simplified circuit diagram of a sensor comprising a one-dimensional array of memristive elements according to another embodiment of invention.

A further embodiment is illustrated in FIG. 6 which comprises a one-dimensional array of memristors (1×n array). In this case all the column wires are connected to the output line to which the load resistance RL is connected, such that the memristors are simply arranged in parallel.

Figure 7:
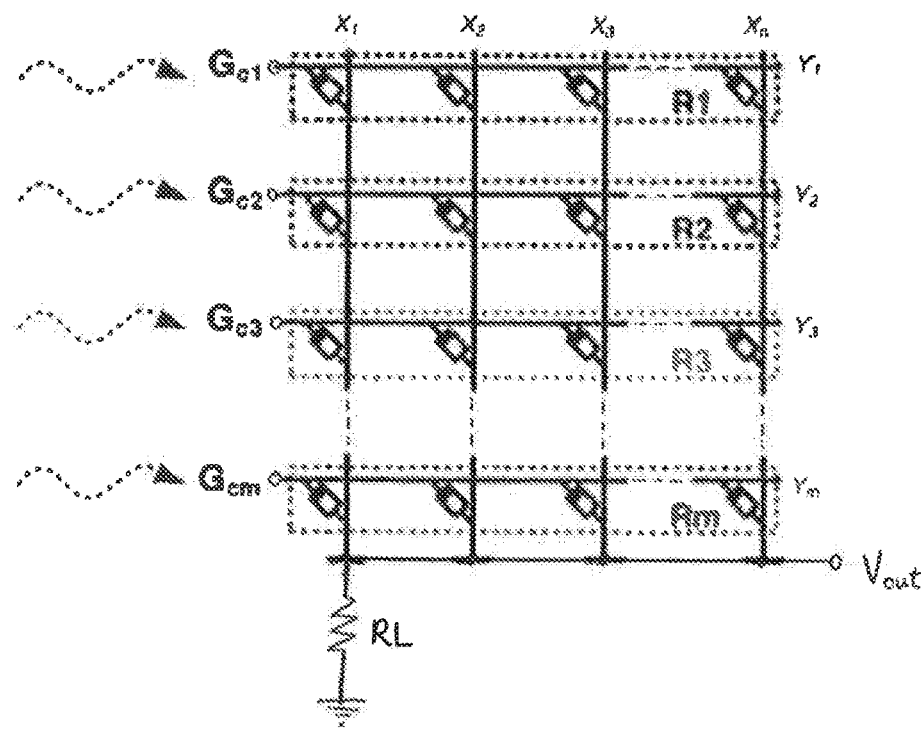
FIG. 7 is a simplified circuit diagram of a sensor comprising multiple one-dimensional arrays of memristive elements, each array for sensing a different species, according to an embodiment of invention.

The structure of FIG. 6 can be expanded in a further embodiment by providing a plurality of one-dimensional arrays. This can be achieved by connecting a two-dimensional array as shown in FIG. 7, such that, in this example, the column wires are shorted together, but the row wires are separate, and can have a read voltage independently applied to each. In a preferred variant, each one-dimensional array is sensitive to a different target species (e.g. a component in a gas to be sensed); this can be achieved by physical or chemical modification of the memristors of that array or of the structures associated with the array. The rows have respective resistances $R_1, R_2, \ldots R_m$. Applying a read voltage to terminal $G_{c1}$ enables the concentration of a first species to be sensed, and the process is sequentially repeated for terminals $G_{c2}$ to $G_{cm}$ to sense the other species. Not all of the rows have to be adapted to sense a unique species; some rows could be duplicated to provide multiple readings of the same species. Although the one-dimensional arrays are shown as rows in this example, they could equivalently be configured as columns.

All of the above embodiments can include control circuitry (not shown) to apply the required voltages, make the necessary connections, measure the output, and provide a sensing function, such as converting the electrical measurement to a gas concentration value or values. The control circuitry can be dedicated logic and hardware, and/or can include general purpose circuitry, such as a microprocessor running suitable software.

Embodiments of the invention can take advantage of highly dense arrays of memristive sensor elements, for example on a microelectronic chip. An array can comprise tens or hundreds of elements, but can also be much larger such as 1024×1024 elements or even more. This makes the sensor compact, robust and low-power. The sensor is particularly suitable for use in portable devices, such as integrating into smart phones, tablet computers, or hand-held sensors.

The invention claimed is:

1. A sensor comprising:
a plurality of sensor elements arranged in an array,
wherein each of the sensor elements is memristive and has an electrical resistance characteristic related to exposure to a species to be sensed,
wherein the sensor elements are arranged to be connectable such that at least one of the sensor elements is connected in parallel with at least one other of the sensor elements;
wherein the array is a two-dimensional array,
a plurality of conductive row wires and a plurality of conductive column wires, with each of the sensor elements connected between one of the conductive row wires and one of the conductive column wires,
including connections to electrically connect multiple ones of the conductive row wires to each other and connections to electrically connect multiple ones of the conductive column wires to each other, and
wherein all of the conductive row wires except a selected one are connected to each other, and all of the conductive column wires except a selected one are connected to each other.

2. The sensor according to claim 1, wherein the connections are switchable and controlled by logic circuitry.

3. The sensor according to claim 1, wherein each of the conductive row wires and each of the conductive column wires is individually addressable.

4. The sensor according to claim 1, wherein the plurality of sensor elements arranged in an array is in a form of a micro-electronic structure.

5. The sensor according to claim 1, further comprising a crossbar architecture connecting the sensor elements arranged in an array.

6. The sensor according to claim 1 provided on a chip.

7. The sensor according to claim 1, wherein the sensor is at least one of a gas sensor, a liquid sensor, and a sensor for sensing a species present in a liquid.

8. A method of reading a sensor, the sensor comprising a plurality of sensor elements arranged in an array, wherein each of the sensor elements is memristive and has an electrical resistance characteristic related to exposure to a species to be sensed, wherein the sensor elements are arranged such that at least one of the sensor elements is connected in parallel with at least one other of the sensor elements, wherein the array is a two-dimensional array, including a plurality of conductive row wires and a plurality of conductive column wires, with each of the sensor elements connected between one of the conductive row wires and one of the conductive column wires, and including connections to electrically connect multiple ones of the conductive row wires to each other and connections to electrically connect multiple ones of the conductive column wires to each other, the method comprising the steps of:

connecting all of the conductive row wires except a selected one to each other;

connecting all of the conductive column wires except a selected one to each other; and measuring an electrical property of the sensor array through the selected one row wire and the selected one column wire.

* * * * *